(12) United States Patent
Sauer

(10) Patent No.: US 7,717,902 B2
(45) Date of Patent: May 18, 2010

(54) CATHETER FOR DRAINAGE OF THE BLADDER

(76) Inventor: Manfred Sauer, Im Neurott 7, 74931 Lobbach (DE)

( * ) Notice: Subject to any disclaimer, the term of this patent is extended or adjusted under 35 U.S.C. 154(b) by 784 days.

(21) Appl. No.: 10/819,583

(22) Filed: Apr. 7, 2004

(65) Prior Publication Data

US 2004/0193143 A1   Sep. 30, 2004

Related U.S. Application Data

(63) Continuation of application No. PCT/DE03/00129, filed on Jan. 17, 2003.

(30) Foreign Application Priority Data

| Mar. 20, 2002 | (DE) | ................................ 102 12 462 |
| Nov. 5, 2002 | (DE) | ................................ 102 51 733 |
| Nov. 20, 2002 | (DE) | ................................ 102 54 242 |
| Dec. 16, 2002 | (DE) | ................................ 102 59 002 |

(51) Int. Cl.
*A61M 5/00* (2006.01)
*A61M 1/00* (2006.01)
*A61M 27/00* (2006.01)

(52) U.S. Cl. ............................. 604/544; 604/8; 604/540

(58) Field of Classification Search ......... 604/540–544, 604/526, 6.16, 264, 910, 915, 270, 8–10, 604/19, 28–29, 36, 93.01–96.01, 104, 117; 256/526; 600/29, 30

See application file for complete search history.

(56) References Cited

U.S. PATENT DOCUMENTS

| 3,599,641 | A | * | 8/1971 | Sheridan ..................... 604/256 |
| 4,188,954 | A | * | 2/1980 | Patel et al. .................. 604/103 |
| 4,237,894 | A | * | 12/1980 | Cohen ........................ 604/104 |
| 4,248,234 | A |   | 2/1981 | Assenza et al. |
| 4,292,270 | A | * | 9/1981 | Hannah et al. ............... 264/320 |
| 4,361,152 | A | * | 11/1982 | Patel ...................... 604/102.01 |
| 4,498,473 | A | * | 2/1985 | Gereg .................... 128/207.15 |
| 4,502,482 | A | * | 3/1985 | DeLuccia et al. ......... 128/207.15 |
| 4,842,590 | A | * | 6/1989 | Tanabe et al. ................ 604/524 |
| 5,049,138 | A | * | 9/1991 | Chevalier et al. ........... 604/265 |
| 5,180,376 | A | * | 1/1993 | Fischell ....................... 604/524 |
| 5,222,949 | A | * | 6/1993 | Kaldany ...................... 604/524 |
| 5,308,318 | A | * | 5/1994 | Plassche, Jr. ................. 604/540 |

(Continued)

FOREIGN PATENT DOCUMENTS

DE   0 384 476 A1 *   2/1990

(Continued)

*Primary Examiner*—Leslie R. Deak
*Assistant Examiner*—Philip R Wiest
(74) *Attorney, Agent, or Firm*—Alston & Bird LLP

(57) ABSTRACT

A catheter for draining urine from the bladder and which is composed of a flexible plastic tube (1) having an insertion aid (2) secured to the insertion end of the tube. Thus the insertion aid and tube may be inserted into the urethra and guided therethrough into the bladder. The tube (1) has at least one orifice (4) in the region adjacent the insertion aid (2). Also, the insertion aid (2) connects with essentially the same diameter to the tube (1) and ends with a rounded head portion (3), whose diameter may be slightly larger than the diameter of the tube (1). The insertion aid may be significantly more flexible as compared to the tube.

26 Claims, 4 Drawing Sheets

U.S. PATENT DOCUMENTS

| | | | |
|---|---|---|---|
| 5,360,414 A * | 11/1994 | Yarger | 604/264 |
| 5,364,340 A * | 11/1994 | Coll | 604/8 |
| 5,599,291 A * | 2/1997 | Balbierz et al. | 604/8 |
| 5,702,373 A * | 12/1997 | Samson | 604/527 |
| 6,358,229 B1 * | 3/2002 | Tihon | 604/170.03 |
| 6,368,317 B2 * | 4/2002 | Chang | 604/544 |
| 6,511,474 B1 * | 1/2003 | Andersen | 604/264 |
| 6,558,350 B1 * | 5/2003 | Hart et al. | 604/104 |
| 6,589,208 B2 * | 7/2003 | Ewers et al. | 604/104 |
| 6,808,520 B1 * | 10/2004 | Fourkas et al. | 604/526 |

FOREIGN PATENT DOCUMENTS

| | | |
|---|---|---|
| DE | 0 795 339 A1 * | 9/1997 |
| DE | 1 149 604 A1 * | 10/2001 |
| EP | 0 384 476 A1 | 8/1990 |
| EP | 0 795 339 A1 | 9/1997 |
| EP | 1 149 604 A1 | 10/2001 |
| WO | WO 96/33763 A2 | 10/1996 |

* cited by examiner

CATHETER FOR DRAINAGE OF THE BLADDER

CROSS REFERENCE TO RELATED APPLICATION

The present application is a continuation of international application PCT/DE03/00129, filed 17 Jan. 2003, and which designates the U.S. The disclosure of the referenced application is incorporated herein by reference.

BACKGROUND OF THE INVENTION

The invention relates to a catheter for draining urine from the bladder of a user, and which is composed of a flexible tube and an insertion aid secured to the insertion end of the tube for inserting it into the urethra and guiding it therethrough into the bladder, and with the tube having at least one orifice in the region adjacent the insertion aid.

The invention further relates to a catheter for draining urine which is composed of a flexible tube for inserting it into the urethra and guiding it therethrough into the bladder, with the tube being made of plastic and having at least one orifice adjacent its insertion or free end or in the region preceding the free end.

For managing incontinence of male persons, in particular in the case of paraplegia, one applies, among other things, the so-called intermittent self-catheterization (ISK), by which the incontinent male person catheterizes himself four to six times a day. To remain continent between catheterization phases, the treating physician normally prescribes a medication that deactivates or sedates the bladder.

However, the known catheters for draining urine are problematic in practice, inasmuch as during the introduction of the catheter into the urethra and while guiding the catheter tip through the urethra into the bladder, it is necessary to overcome pockets, folds, bends, or the like. If one pushes the catheter with a corresponding force against the existing impediments in the urethra, one will face a considerable risk of injury For example, in the art, one may refer to EP 0 384 476 BE1, which provides as an insertion aid a very special catheter tip. While this catheter tip is made flexible or elastic, it conically tapers toward its free end, and is rounded at its front or free end. Although this specific configuration permits pushing the catheter through the urethra into the bladder, while overcoming the aforesaid problem locations, it also presents in this instance a significant risk of injury because of the necessary application of force.

It is therefore an object of the present invention to improve and further develop a catheter, in particular a disposable catheter, in such a manner that it is easy to be handled by the user, and which reduces the normal risk of injury quite considerably, when being pushed into and through the urethra.

SUMMARY OF THE INVENTION

The above and other objects and advantages are achieved by the provision of a catheter wherein the insertion aid has a rear portion adjacent the tube which has substantially the same outer diameter as the outer diameter of the tube, and a rounded head portion of a diameter slightly larger than the diameter of the tube. Also, the tube includes at least one orifice adjacent the insertion aid.

In accordance with the invention, it has been found that quite contrary to the existing state of the art, the insertion aid connects with essentially the same diameter to the tube, and ends with a rounded head portion, which has at least a slightly larger diameter than the diameter of the tube. With that, it is accomplished that when being introduced into the urethra, the catheter tip expands the urethra at least slightly because of its configuration with the rounded, spherical head portion, so that pockets, folds, and bends are essentially simpler to overcome than has been the case with a tapered tip. In this connection, it has been found that the necessary application of force for inserting the catheter is substantially less than in the case of conventional catheters, thereby reducing again the risk of injury to a very considerable extent. Finally, the catheter of the invention is excellently suited for self-catheterization, even when the handling of the catheter is rendered difficult because of a handicap of the user.

In an advantageous manner, the insertion aid is made of a material similar to that of the tube, with the insertion aid having as a whole a lesser firmness than the tube. Specifically, it would be possible to make the insertion aid half as firm, as measured by its flexural modulus, as the tube for purposes of facilitating the introduction of the tube by means of the insertion aid and for reducing the risk of injury in this process.

Both the insertion aid and the tube could become constantly or stepwise more flexible toward the free end or end on the insertion side. In this case, the tube and/or the insertion aid are made more flexible than the remaining tube over a length of 5 to 10 cm from the free end.

The tube and the insertion aid could both be made of plastic, in particular PVC. In this connection, it will be of a very special advantage, when the tube and/or the insertion aid are chemically treated, preferably by means of plasticizers, for obtaining constantly more flexible regions toward the free end. The treatment with plasticizers assists the manufacture of the catheter to the extent that both the tube and the insertion aid consist of PVC, and that both parts are interconnected in a material engaging relationship by a mutual diffusion of plasticizers.

For an unimpeded drainage of the urine, the tube preferably includes at least one, and possibly two or more orifices. In a further advantageous manner, these orifices are formed directly behind the insertion aid. They are formed, for example, by a punching operation. In a further advantageous manner, the orifices are at least outwardly rounded to avoid sharp edges in their edge region. Such a rounding of the orifice can be realized by a temperature treatment of the area that includes the orifice. In this process, the material softens and forms, because of the resultant surface tension, a rounded surface in the region of the edge of the orifice, so that the risk of injury is also reduced in this respect.

It is likewise possible to treat at least the region of the tube or the region of the insertion aid that is used for the insertion, such that it promotes the wetting behavior in comparison with a conventional lubricant. Such a treatment may occur chemically and/or mechanically. In any case, such a treatment accomplishes that the lubricant adheres to the outside wall of the tube and/or the insertion aid in a better way, so that the introduction of the tube into the urethra is also assisted to this extent.

In a second embodiment of the catheter of the present invention, the tube has an insertion end portion adjacent the insertion end which is more flexible than the remaining portion of the tube. In accordance with this embodiment of the invention, it has been found that it is likewise possible to insert a conventional catheter into the urethra and guide it therethrough effortlessly and with a reduced risk of injury, when it is of a very special quality in its front region, i.e., in the region of its end on the insertion side. Thus, the tube is made more flexible in the region of its insertion end than in the region preceding it.

In this connection, it is of very special importance that the tube exhibits a firmness or stiffness that is needed for its insertion into the urethra. To overcome curved tracts, the tube is made more flexible in its front region, so that it can adapt to anatomical situations as the insertion continues. Moreover, the more flexible realization of the tube in the region of its end on the insertion side sees to it that the risk of injuries is effectively avoided.

In a particularly advantageous manner, the tube is made in the region of its end on the insertion side not only slightly, but also considerably more flexible than in the region that precedes it. To this end, the tube is provided in its front region with a very flexible "tip," which easily adapts itself to the urethra. The pressure that is needed for an insertion or passage is exerted via the rear, relatively firm portion of the flexible tube.

In quite an advantageous manner, the tube becomes constantly or stepwise more flexible toward its end on the insertion side. In other words, the tube comprises at its end on the insertion side, zones of differing rigidity. In this case the front or free end is understood to be the most flexible zone.

As previously described, the tube may be a simple tube, whose front end is open. An edge defining the opening should be rounded, for example, by a temperature treatment, so that the risk of injury is effectively reduced also in this region. Within the scope of a further embodiment, it is possible to form at the end on the insertion side of the tube, a special insertion aid for inserting the tube into the urethra and guiding it therethrough into the bladder.

Within the scope of such an embodiment, the insertion aid connects with the same diameter to the tube, and ends with a rounded or ball-shaped head portion, which has at least a slightly larger diameter than the diameter of the tube. With that, it is accomplished that when inserting the catheter tip into the urethra, the urethra expands at least slightly because of the configuration of the round, ball-shaped head portion, so that pockets, folds, and bends are substantially simpler to overcome than is the case with a tapered tip. Furthermore, it is essential that the necessary application of force for inserting the catheter is substantially simpler than in conventional catheters, whereby the risk of injury is again reduced to a very considerable extent. Finally, the embodiment under discussion is excellently suited for self-catheterization, even when handling of the catheter is difficult by reason of a handicap of the user.

It is likewise possible to make the diameter of the head portion slightly smaller than the diameter of the tube, or however, also identical with the diameter of the tube.

In a further advantageous manner, the insertion aid is made of a material similar to that of the tube. As a whole, the insertion aid may have a lesser firmness than the tube. As a specific example, the insertion aid could be made at least half as firm as the tube for facilitating the insertion of the tube by means of the insertion aid and for reducing the risk of injury when handling it.

Toward the free end or toward the end on the insertion side, it would be possible to make the insertion aid constantly or stepwise more flexible in the same way as also applies to the tube without an insertion aid. For example, it would be possible to make the insertion aid more flexible than the remaining tube over a length of 5 to 10 cm from the free end. The same applies to the embodiment without an insertion aid, namely to the region of the tube end on the insertion side.

The tube and, if need be, the insertion aid could be made of a plastic material, such as PCV. In this connection, it will be of special advantage, when the tube and/or the insertion aid are chemically treated, in particular by means of plasticizers, so as to obtain constantly more flexible regions toward the free end. The treatment with plasticizers assists the manufacture of the catheter in that both the tube and, if need be, the insertion aid consist of PVC, and that both components are interconnected in a material engaging relationship by a mutual diffusion of plasticizers.

The arrangement of a spherical insertion aid requires special orifices to be able to take in body fluid. To this end, two or more orifices are provided in the tube. In a further advantageous manner, these orifices are formed directly behind the insertion aid. They are made, for example, by a punching operation. In a further advantageous manner, the orifices are at least outwardly rounded to avoid sharp edges in their region. The rounding of the orifice can be realized by a temperature treatment of the region comprising the orifice. In this process, the material softens and forms because of the resultant surface tension, a rounded surface in the region of the edge of the orifice, so that the risk of an injury is also prevented in this respect.

Finally, it is possible to treat at least the region of the tube or the insertion aid that is used for insertion in such a manner that the treatment assists the wetting behavior in comparison with a conventional lubricant. Such a treatment may occur chemically and/or mechanically. In any case, a corresponding treatment accomplishes that the lubricant adheres to the outside wall of the tube and/or the insertion aid in a better way, so that it assists the insertion of the tube into the urethra likewise to this extent.

There exist various possibilities of improving and further developing the teaching of the present invention in an advantageous manner. To this end, one may refer to the following description of embodiments with reference to the drawings. In conjunction with the description of preferred embodiments of the invention with reference to the drawings, also generally preferred improvements and developments of the teaching are described.

DETAILED DESCRIPTION OF THE PREFERRED EMBODIMENTS

Figure 1:
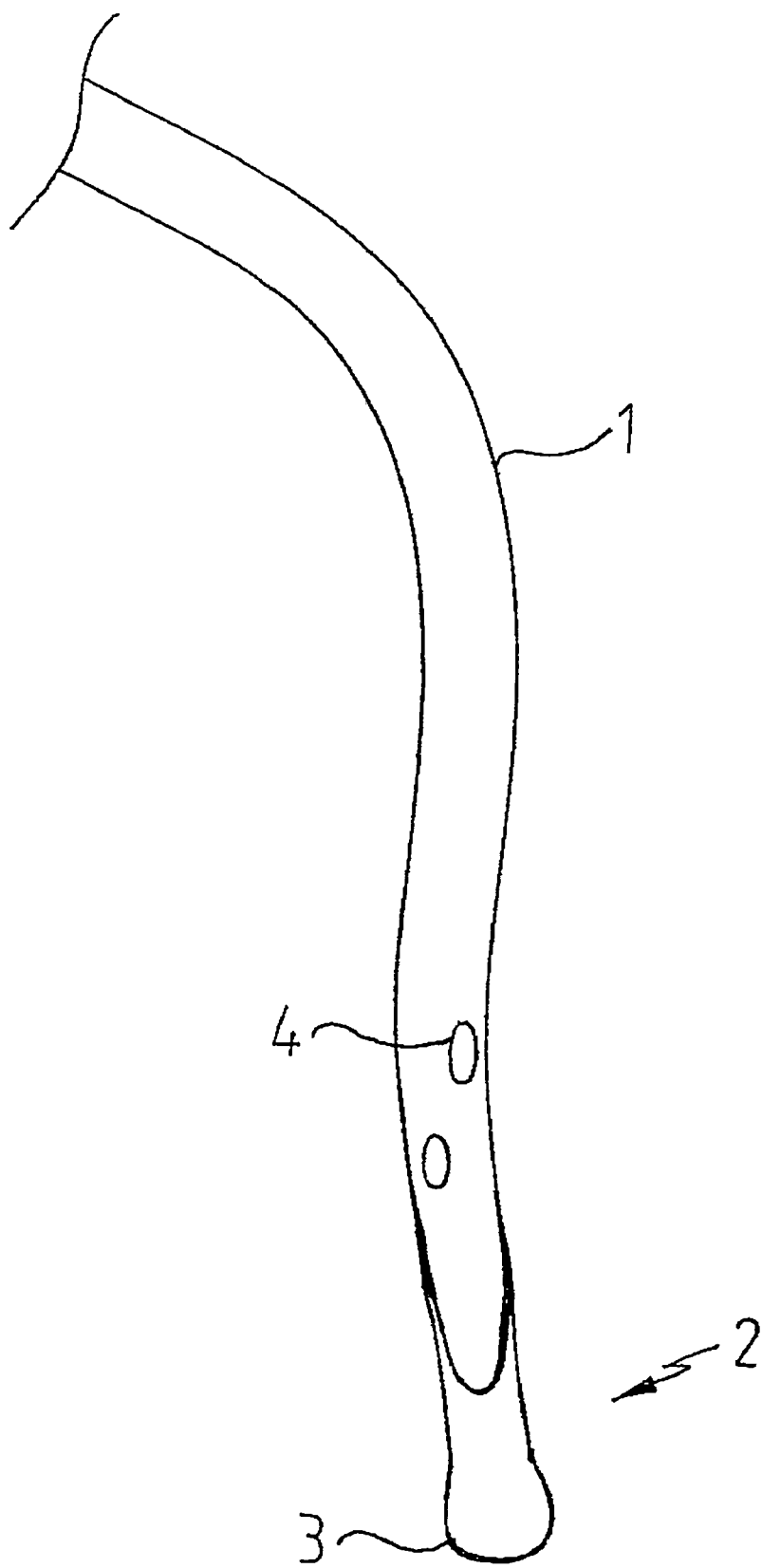
FIG. 1 is a schematic view of a first embodiment of a catheter according to the invention and with a rounded tip.

FIG. 1 illustrates an embodiment of a catheter according to the invention. For the sake of simplicity, the Figure shows only a flexible tube 1 with an insertion aid 2. The insertion aid 2 is arranged at the insertion end of the tube 1, and there secured to the tube 1. The insertion aid 2 is thus made integral with the tube 1, with the insertion aid 2 being substantially more flexible than the tube 1.

In accordance with the invention, the rear portion of the insertion aid 2 has essentially the same diameter as the tube 1, and connects accordingly to the tube 1 in a material engaging relationship. A head portion 3 of the insertion aid 2 is made rounded, i.e. spherical or ball-shaped, and has at least a slightly larger diameter than the diameter of the tube 1, which results in the above-described advantages.

As further shown in FIG. 1, the tube 1 includes orifices 4 for draining urine, with the selected embodiment comprising a total of two orifices 4. For a faster drainage of urine, it is also possible to provide additional orifices 4. The peripheral edges of the orifices 4 are rounded for precluding as much as possible the risk of an injury during an insertion through the urethra.

Figure 2:
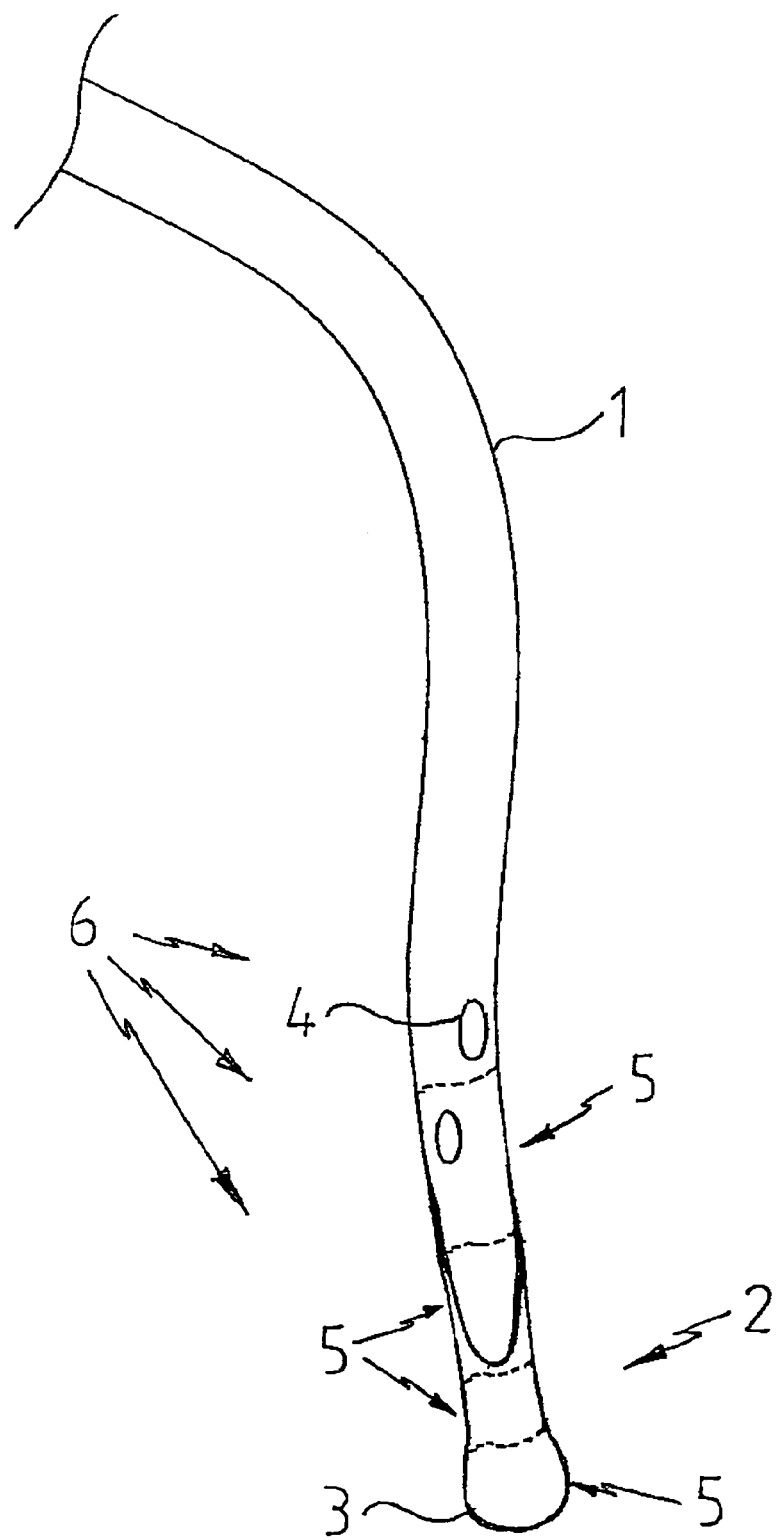
FIG. 2 is a schematic view of a second embodiment of a catheter according to the invention with a rounded tip and indicated zones of different flexibility.

In the embodiment shown in FIG. 2, the insertion aid 2 and the end of the tube 1 on the insertion side are made with zones 5 of differing flexibility, so that they again assist in achieving a gentle insertion of the catheter. Furthermore, FIG. 2 indicates a region 6, which provides a very excellent adhesion of a lubricant as a result of a chemical treatment.

Figure 3:
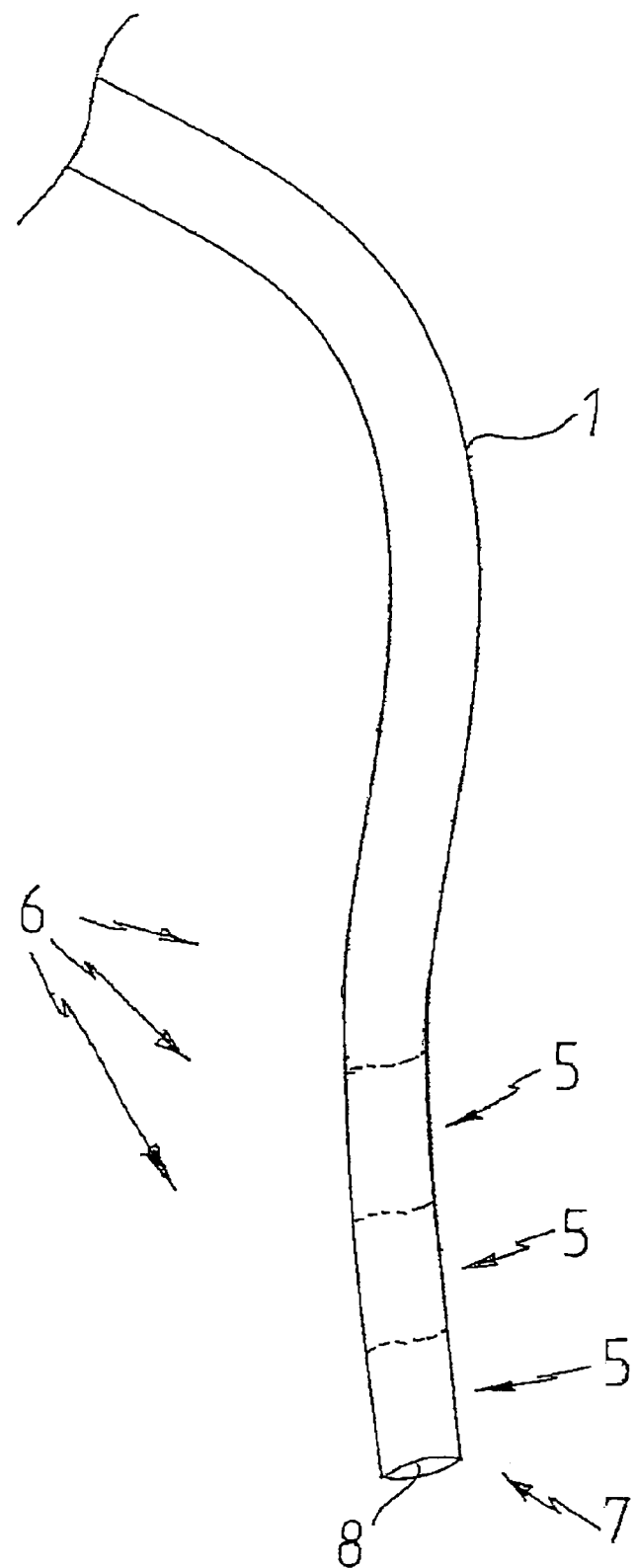
FIG. 3 is a schematic view of a third embodiment of a catheter according to the invention with a uniform, open insertion aid and indicated zones of different flexibility.

In a further embodiment, FIG. 3 shows a catheter for draining urine, which comprises a flexible tube 1 for inserting the catheter into the urethra and guiding it therethrough into the bladder. The tube 1 is made of plastic, more specifically of PVC, and has at its free end 7 an orifice 8, which is formed by the end of the tube 1.

In accordance with the invention, the tube 1 is made more flexible in the region of its end on the insertion side, i.e. at its free end 7, than in the region preceding it. In the specifically selected embodiment, zones 5 of different flexibility or rigidity are provided, so as to assist respectively the insertion into the urethra and the passage through the urethra into the bladder.

FIG. 3 further indicates that a special region 6 is provided, which is chemically treated, so that, in the region 6, a lubricant adheres especially well to the outside wall of the tube 1.

Figure 4:
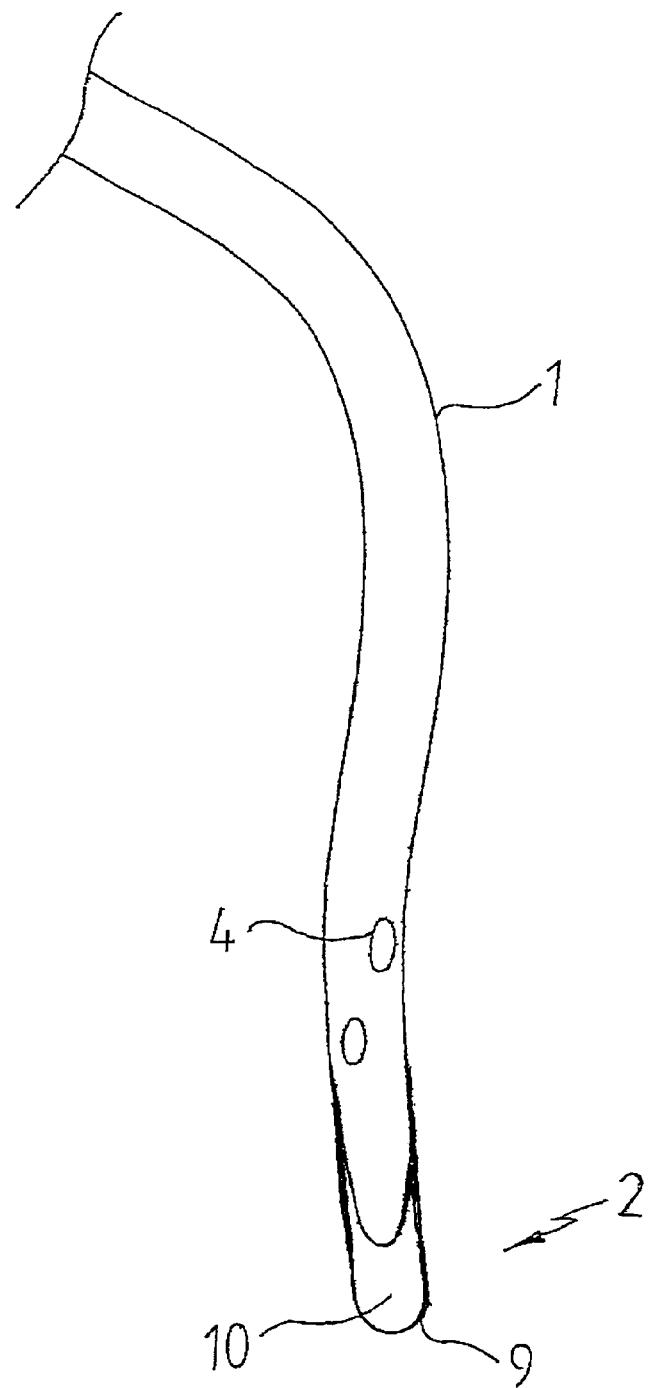
FIG. 4 is a schematic view of a fourth embodiment of a catheter with a uniform and rounded insertion aid.

FIG. 4 shows a fourth embodiment of a catheter according to the invention. For the sake of simplicity, only the flexible tube 1 and a special insertion aid 2 are illustrated. The insertion aid 2 is arranged or secured to the tube 1 at an end 9 on the insertion side of the tube 1. Specifically, it has a round head 10, which forms the front end of the insertion aid 2. In this connection, it is possible to provide the region of the insertion aid 2 with zones of different flexibility, as is the case in the embodiment shown in FIG. 1.

Many modifications and other embodiments of the inventions set forth herein will come to mind to one skilled in the art to which these inventions pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A catheter for draining urine from the bladder of a user, comprising:
    a flexible tube which comprises a peripheral wall and which defines an insertion end, an insertion aid being integrally formed with the insertion end of the tube for guiding the tube through the urethra and into the bladder, said insertion aid having a rear portion adjacent the tube which has substantially the same outer diameter as the outer diameter of the tube, and a rounded head portion at a front end of the insertion aid having a diameter larger than the diameter of the tube and the rear portion, wherein at least a portion of the rear portion has a length that is greater than the diameter of the rounded head portion and has an outer diameter that is substantially the same as the outer diameter of the tube along its entire length,
    wherein the rounded head portion comprises a massive material having less firmness than the tube, and
    wherein said tube includes at least one orifice extending through the peripheral wall of the tube and spaced rearwardly behind the insertion aid so that the orifice does not pass through the rounded head portion or the rear portion of the insertion aid.

2. The catheter of claim 1 wherein the tube and the insertion aid are both composed of a plastic material, and wherein the insertion aid exhibits less firmness than does the tube.

3. The catheter of claim 2 wherein the firmness of the insertion aid is about one half the firmness of the tube.

4. The catheter of claim 1 wherein the head portion of the insertion aid is less firm than is the rear portion thereof.

5. The catheter of claim 1 wherein the tube defines an insertion end portion which terminates in said insertion end, and wherein the insertion end portion becomes progressively or stepwise less firm toward said insertion end.

6. The catheter of claim 5 wherein the insertion end portion of the tube has a length of about 5 to 10 cm from said insertion end, and wherein the insertion end portion is less firm than the remaining portion of the tube.

7. The catheter of claim 1 wherein the tube and the insertion aid are both composed of a plastic material, and wherein the tube defines an insertion end portion which terminates in said insertion end, and wherein the insertion end portion of the tube and/or the insertion aid are chemically treated with a plasticizer to soften the material thereof.

8. The catheter of claim 1 wherein the tube and the insertion aid are both composed of a plastic material, and wherein the insertion aid is connected to the tube in a material engaging relationship by a mutual diffusion of plasticizers.

9. The catheter of claim 1 wherein the at least one orifice is formed by a punching operation and has outwardly rounded edges.

10. The catheter of claim 9 wherein the outwardly rounded edges are formed by an elevated temperature treatment.

11. The catheter of claim 1 wherein the tube defines an insertion end portion which terminates in said insertion end, and wherein the insertion end portion of the tube and or the insertion aid are mechanically or chemically treated for assisting a wetting behavior toward lubricants.

12. The catheter of claim 1 wherein the rear portion of said insertion aid extends from the rounded head portion in a direction aligned with the tube, and wherein the rear portion and the insertion end of the tube are in a materially engaging relationship such that the outer diameter of the rear portion is substantially the same as the outer diameter of the tube along the entire length of the rear portion.

13. The catheter of claim 1 wherein the insertion aid is free of any orifices communicating with the exterior surface thereof such that the exterior surface is smooth and uninterrupted.

14. A catheter for draining urine from the bladder of a user, comprising
    a flexible plastic tube consisting solely of a polymeric material and defining an insertion end, said tube including an orifice adjacent said insertion end, and wherein the tube has an insertion end portion adjacent said insertion end which is less firm than the remaining portion of the tube; and an insertion aid connected to the insertion end of the tube for guiding the tube through the urethra and into the bladder, said insertion aid having a rear portion adjacent the tube which has substantially the same outer diameter as the outer diameter of the tube, and a rounded head portion comprising a massive material having less firmness than the tube, wherein at least a portion of the rear portion has a length that is greater than a diameter of the rounded head portion and has an outer diameter that is substantially the same as the outer diameter of the tube along its entire length.

15. The catheter of claim 14 wherein the insertion end portion of the tube becomes progressively or stepwise less firm toward said insertion end.

16. The catheter of claim 14 wherein the insertion end of the tube is open to define said orifice.

17. The catheter of claim 16 wherein the open end of the tube has outwardly rounded edges.

18. The catheter of claim 14 wherein the diameter of the rounded head portion is slightly less than the diameter of the tube.

19. The catheter of claim 14 wherein the diameter of the rounded head portion is about the same as the diameter of the tube.

20. The catheter of claim 14 wherein the diameter of the rounded head portion is slightly greater than the diameter of the tube.

21. The catheter of claim 14 wherein the tube and the insertion aid are both formed of a plastic material, and wherein the insertion aid exhibits less firmness than does the tube.

22. The catheter of claim 21 wherein the firmness of the insertion aid is about one half the firmness of the tube.

23. The catheter of claim 14 wherein the head portion of the insertion aid is less firm than is the rear portion thereof.

24. The catheter of claim 14 wherein the insertion end portion has a length of about 5 to 10 cm from said insertion end.

25. The catheter of claim 14 wherein the insertion end portion of the tube and/or the insertion aid are formed of a plastic material which has been chemically treated to soften the material thereof.

26. The catheter of claim 14 wherein the tube and the insertion aid are both composed of a plastic material, and wherein the insertion aid is connected to the tube in a material engaging relationship by a mutual diffusion of plasticizers.

* * * * *